(12) United States Patent
Rudmann et al.

(10) Patent No.: US 8,730,480 B2
(45) Date of Patent: May 20, 2014

(54) TESTING OF OPTICAL DEVICES

(71) Applicant: Heptagon Micro Optics Pte. Ltd., Singapore (SG)

(72) Inventors: Hartmut Rudmann, Jona (CH); Matthias Gloor, Rueschlikon (CH)

(73) Assignee: Heptagon Micro Optics Pte. Ltd., Singapore (SG)

( * ) Notice: Subject to any disclaimer, the term of this patent is extended or adjusted under 35 U.S.C. 154(b) by 0 days.

(21) Appl. No.: 14/076,820

(22) Filed: Nov. 11, 2013

(65) Prior Publication Data

US 2014/0070817 A1  Mar. 13, 2014

Related U.S. Application Data

(63) Continuation of application No. PCT/SG2013/000371, filed on Aug. 26, 2013.

(60) Provisional application No. 61/768,775, filed on Feb. 25, 2013, provisional application No. 61/700,189, filed on Sep. 12, 2012.

(51) Int. Cl.
*G01N 21/55* (2014.01)
*G01D 18/00* (2006.01)

(52) U.S. Cl.
CPC .............. *G01N 21/55* (2013.01); *G01D 18/00* (2013.01)
USPC .............. 356/445; 356/239.1; 250/252.1; 250/493.1; 359/819; 359/820

(58) Field of Classification Search
CPC .................. G01N 21/55; G01D 18/00
USPC ............ 356/445, 239.1, 213–218; 324/754, 324/755, 756, 765; 359/819, 820, 823; 250/252.1, 353, 342, 493.1, 522.1
See application file for complete search history.

(56) References Cited

U.S. PATENT DOCUMENTS

| | | | |
|---|---|---|---|
| 4,451,785 A | 5/1984 | Rozniecki et al. | |
| 5,350,923 A | 9/1994 | Bassignana et al. | |
| 5,631,571 A | 5/1997 | Spaziani et al. | |
| 5,684,596 A * | 11/1997 | Eslinger et al. | 356/614 |
| 6,337,871 B1 | 1/2002 | Choa | |
| 6,428,650 B1 * | 8/2002 | Chung | 156/250 |

(Continued)

FOREIGN PATENT DOCUMENTS

EP  1408343 A1  4/2004

OTHER PUBLICATIONS

Australian Patent Office, International Search Report and Written Opinion in application No. PCT/SG2013/000371 (dated Dec. 2, 2013).

*Primary Examiner* — Sang Nguyen
(74) *Attorney, Agent, or Firm* — Fish & Richardson P.C.

(57) ABSTRACT

The present disclosure describes techniques for testing optical devices in a manner that, in some implementations, simulates the environment in which the devices will be used when they are integrated into the end-product or system. For example, one aspect includes providing a transparent sheet that is positioned near the optical device in a manner that simulates at least some aspects of the environment when the device is incorporated into the end-product or system. The testing can be performed, for example, while the optical devices are in production or at some other time prior to their being integrated into an end-product or system.

9 Claims, 4 Drawing Sheets

(56) References Cited

U.S. PATENT DOCUMENTS

| | | |
|---|---|---|
| 6,608,293 B2 | 8/2003 | Kuderer |
| 6,836,135 B2 | 12/2004 | Harris et al. |
| 7,109,739 B2 | 9/2006 | Gothoskar et al. |
| 7,184,626 B1 | 2/2007 | Gunn, III et al. |
| 7,245,378 B2 * | 7/2007 | Kwan et al. .................. 356/432 |
| 7,378,646 B2 | 5/2008 | Sherrer |
| 7,504,823 B2 | 3/2009 | Rumbaugh |
| 7,599,049 B2 | 10/2009 | Huang et al. |
| 7,859,675 B2 | 12/2010 | Maryfield et al. |
| 7,929,227 B2 * | 4/2011 | Bieg et al. .................... 359/819 |
| 2001/0021287 A1 | 9/2001 | Jewell et al. |
| 2004/0008342 A1 * | 1/2004 | Hutt et al. ................. 356/239.1 |
| 2004/0169520 A1 | 9/2004 | Larikova et al. |
| 2005/0265717 A1 | 12/2005 | Zhou |
| 2008/0239317 A1 * | 10/2008 | Schulkin et al. .............. 356/365 |
| 2009/0156905 A1 | 6/2009 | Ries et al. |
| 2009/0165549 A1 | 7/2009 | Grass et al. |
| 2011/0006226 A1 * | 1/2011 | Schulkin et al. ........... 250/493.1 |
| 2012/0235029 A1 | 9/2012 | Tam |

* cited by examiner

TESTING OF OPTICAL DEVICES

CROSS-REFERENCE TO RELATED APPLICATIONS

This application is a continuation of International Application No. PCT/SG2013/000371 filed on Aug. 26, 2013, which claims the benefit of priority of U.S. application Ser. No. 61/700,189, filed on Sep. 12, 2012, and U.S. application Ser. No. 61/768,775, filed on Feb. 25, 2013. The disclosures of the prior applications are incorporated herein by reference.

TECHNICAL FIELD

This disclosure relates to automated testing of optical devices.

BACKGROUND

Various types of optical devices are incorporated into a wide range of consumer and industrial products and systems. One such device is an optical proximity sensor, which can be integrated, for example, into a mobile, hand-held cell phone. The proximity sensor can be used to sense whether the cell phone is held close to the user's ear (e.g., during a phone call) and to cause the phone's display to switch off so as to reduce power consumption or to prevent unintended activation of icons on the screen. If the phone is moved away from the user's ear, the proximity sensor can detect that situation and cause the display to switch on and allow icons to be activated.

Testing of such optical devices is important to ensure that they function properly and satisfy any required specifications. In general, it can be advantageous to test the optical devices after they are integrated into the end-products so as to allow the devices to be tested in the environment in which they will be used. On the other hand, doing so can increase overall cost and result in the need to remove devices that do not meet the tests in a satisfactory way.

SUMMARY

The present disclosure describes techniques for testing optical devices in a manner that, in some implementations, simulates the environment in which the devices will be used when they are integrated into the end-product or system. For example, one aspect includes providing a transparent sheet that is positioned near the optical device in a manner that simulates at least some aspects of the environment when the device is incorporated into the end-product or system. The testing can be performed, for example, while the optical devices are in production or at some other time prior to their being integrated into an end-product or system. In some implementations, the transparent sheet and other features of the testing unit are designed so that the test environment mimics aspects of the situation in which the optical device is integrated into a cell phone (e.g., where the optical device is located within a cavity of the cell phone that is covered by a transparent cover that protects the device from dirt, dust, moisture and the like).

The techniques described here can be used, for example, in connection with various types of optical devices, including opto-electronic modules, sensors such as, e.g., ambient light sensors, proximity sensors, array cameras, computational cameras and other multi-channel optical devices and apparatuses. The optical devices may be, for example, micro-optics devices or modules and can include at least one active optical component and/or at least one passive optical component. The devices and modules may be of other types as well. The techniques can be particularly useful in connection with the testing of optical proximity sensors designed for cell phones and the like.

The disclosure also describes a testing unit for implementing the disclosed techniques.

In one aspect, for example, the disclosure describes an automated method of testing an optical device. The method can include placing the optical device on or in close proximity to a transparent sheet, causing the optical device to emit light through the transparent sheet, analyzing a response of the optical device after it emits the light, and determining in a processing unit whether or not the optical device passes a test based at least in part on analyzing the response of the optical device.

Another aspect describes an automated method of testing an optical device that is on or in close proximity to a transparent sheet. The method can include causing the optical device to emit light that is transmitted through the transparent sheet into a region that has a back wall having a first reflectivity, and analyzing a first response of the optical device. The method also includes causing a second surface to be moved into the region such that the second surface intersects an optical axis of the optical device, wherein the second surface has a reflectivity different from the back wall. Subsequently, the optical device is caused to emit light that is transmitted through the transparent sheet into the region, and a second response of the optical device is analyzed. The method further includes using a processing system to determine whether or not the optical device passes a test based at least in part on analyzing the responses of the optical device.

According to another aspect, a testing unit for testing an optical device is described. The testing unit can include a device holder to hold the optical device, a testing electronics module adjacent the device holder, and a transparent cover adjacent the device holder. The testing electronics module includes electrical contacts for connection to electrical contacts of the optical device and including electronics to measure a response of the optical device. The testing unit further includes a wall located on a side of the transparent cover opposite that of the device holder and having a first reflectivity. A movable partition is slidable in and out of the region and has a reflectivity different from the wall. A processing unit is configured to generate a control signal to cause the optical device to emit light that is transmitted through the transparent sheet toward the wall, analyze a first response of the optical device, generate a control signal to cause the movable partition to be moved between the wall and the transparent cover, generate a control signal to cause the optical device to emit light that is transmitted through the transparent cover toward the movable partition, analyze a second response of the optical device, and determine whether or not the optical device passes a test based at least in part on analyzing the responses of the optical device.

In some implementations, the wall is composed of a black reference card, and the partition is composed of a grey reference card, both of which can have well-defined reflectance properties. The black reference card can be used, for example, for measuring leakage between a light emitting element and light detecting element in the optical device, and for calibrating the measurement. The grey reference card can be used, for example, for measuring the optical response of the optical device against a surface with well-defined reflectance properties.

Other aspects, features and advantages will be readily apparent from the following detailed description, the accompanying drawings, and the claims.

DETAILED DESCRIPTION

Figure 1:
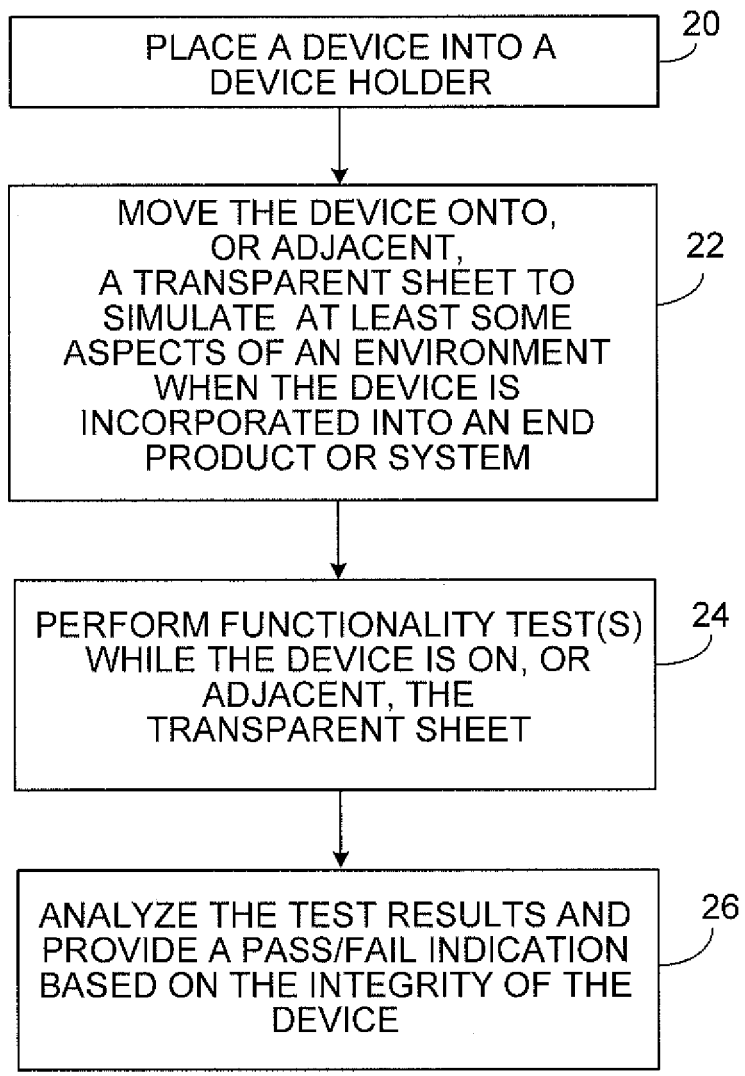
FIG. 1 is a flow chart of a method of testing an optical device.

As indicated by FIG. 1, some implementations include an automated method of testing optical devices. The method can include placing one or more devices into a device holder to test the functionality of each device under specified conditions in accordance with particular specifications (block 20). An automated pick-and-place machine can be used, for example, to place the devices into the device holder. The method can include moving the devices, one at a time, onto, or adjacent, a transparent sheet so as to simulate particular features of an environment when the device is incorporated into an end product or system (block 22). While the device is on, or adjacent, the transparent sheet, one or more tests are performed (block 24). The tests can include, for example, directing optical signals from the optical device through the transparent sheet, and/or detecting, in the optical device, optical signals that pass back through the transparent sheet. The test results then can be analyzed, and a pass/fail indication can be provided based on the integrity of the individual device (block 26).

Figure 2:
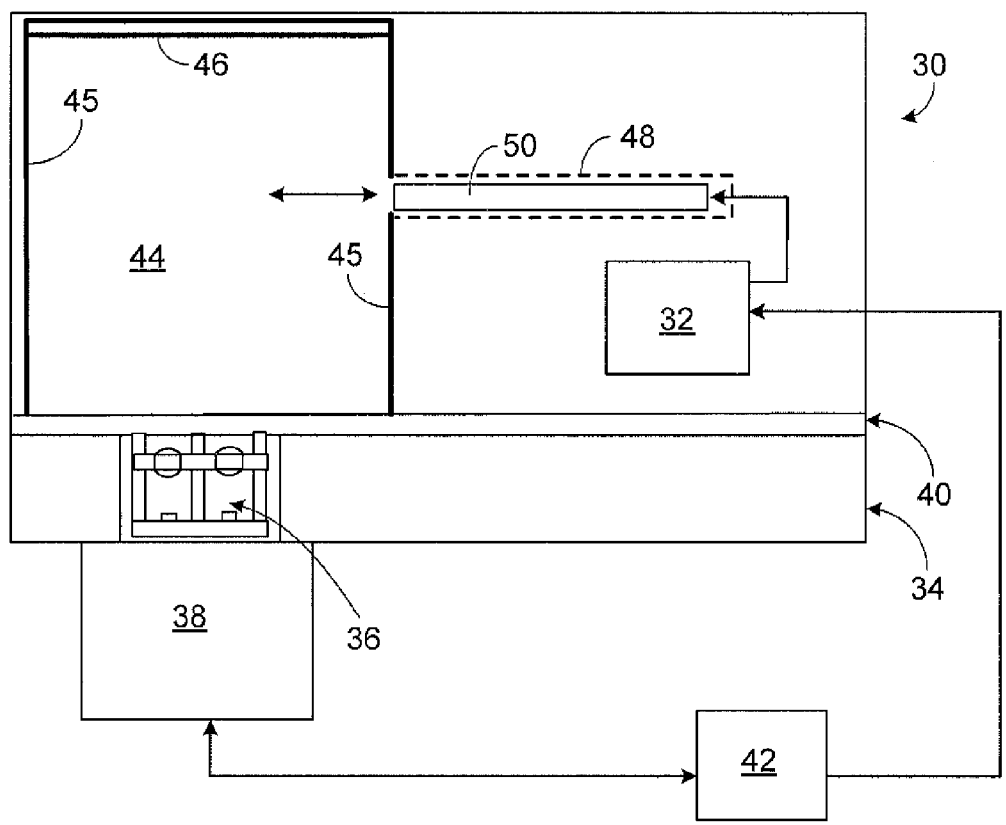
FIG. 2 is a diagram of an optical device testing unit showing a partition in a first position.

An example of a testing unit 30 is illustrated in FIG. 2. Testing unit 30 includes a device holder 34, which, in some implementations, can hold multiple optical devices. For example, in the illustrated implementation, device holder 34 can hold up to sixteen optical devices. In other implementations, device holder 34 may be capable of holding a greater or lesser number of optical devices. The use of holder 34 to hold the device(s) in an accurate position can facilitate ensuring that good electrical contacts are provided for the testing. Furthermore, the techniques described here can facilitate fast testing of the devices because multiple devices can be tested simultaneously.

As shown in FIG. 2, an optical device 36 can be positioned in device holder 34. Optical device 36 can include, for example, one or more active and/or passive optical components. Examples of an active optical component include a light sensing or a light emitting component, such as a photodiode, an image sensor, an LED, an OLED, a laser chip, an optical transmitter die including, for example, a light-emitting diode (that emits, e.g., infrared light or near-infrared light) or an optical receiver die including, for example, a photo diode for detecting, e.g., infrared light or near-infrared light). Examples of passive optical components include an optical component that redirects light by refraction and/or diffraction and/or reflection such as a lens, a prism, a mirror or an optical system (e.g., a collection of passive optical components that may include mechanical elements such as aperture stops, image screens or holders). The various optical components may be mounted on or over a substrate.

In the illustrated example, optical device 36 is a proximity sensor that includes both a light emitting component as well as a light sensing component mounted on a common substrate and separated from one another by a opaque partition. Lenses or other optics are aligned above each of the light emitting and light sensing components to help focus the light to and from optical device 36. During use, light emitted from optical device 36 by the light emitting component can be reflected by a surface outside of the optical device, and a portion of the reflected light can be detected by the light sensing component. When the proximity sensor is installed, for example, in a mobile phone, the amount of reflected light can be use, in known manner, to detect that the mobile phone is next to the user's ear or face so that the phone's display can be dimmed or deactivated automatically when the display is not being used, thereby extending the life of the phone's battery and preventing unintended activation of the displayed icons. Optical device 36 also can include external electrical contacts, such as solder balls or SMT contacts, on the underside of the substrate, that provide an electrical path for signals to and from the light emitting and light sensing components.

When optical device 36 is positioned in device holder 34, external electrical contacts (e.g., SMT pads or solder balls) of the optical device should be in contact with a testing electronics module 38, which includes electrical contacts for connection to the external electrical contacts of optical device 36. It is, therefore, important for optical devices to be positioned into device holder 34 with a high degree of accuracy. In some implementations, an optical device may need to be placed in device holder 34 with an accuracy to within several hundred microns (e.g., 100-300 μm).

Testing electronics module 38 also can include, for example, a signal amplifier or other electronics to measure the response (e.g., optical cross talk) of optical device 36 when light emitted by the optical device is reflected back into the optical device by different surfaces. For example, testing electronics module 38 can provide signals to cause the light emitting component in optical device 36 to emit light, and can receive signals from optical device 36 indicative of the amount of light detected by the light sensing component. Testing electronics module 38 can be coupled to a processing unit 42, such as a personal computer or laptop, which provides control signals to the testing electronics module and and receives output signals indicative of the measurements made by the testing electronics module.

Testing unit 30 also includes a transparent sheet 40 disposed over the top of device holder 34. Transparent sheet 40 can be composed, for example, of any suitable transparent material (e.g. glass, polymer or other crystalline transparent material). The material and thickness of transparent sheet 40 can be chosen to be similar to the material and dimensions of the transparent cover that forms part of the casing of the end-product (e.g., mobile phone) into which the device is to be incorporated. When an optical device 36 is placed in device holder 34 and is positioned over testing electronics module 38, the top of the optical device will be in contact with, or adjacent, one side of transparent sheet 40. On the other side of transparent sheet 40, directly opposite optical device 36, is a space 44. The interior back wall 46 of space 44 (i.e., the wall that faces transparent sheet 40) can be composed of, or covered with, a black material that has well-defined reflectance and absorption properties. Back wall 46 preferably should absorb substantially all light that impinges on it and should reflect little, if any, light. In some implementations, commercially available black reference cards, such as the type used in digital photography, can be used to cover interior walls 46. Examples of such black reference cards are commercially available, for example, from Opteka™. The black reference card at back wall 46 can be used for measuring leakage between a light emitting element and light detecting element in optical device 36, and for calibrating the measurement. Side interior walls 45 of space 44 (i.e., the walls that are substantially perpendicular to transparent sheet 40) also can be composed of, or covered with, a material that absorbs substantially all radiation from the light emitting component in optical device 36. However, side walls 45 need not have well-defined reflectance and absorption properties as does back wall 46. For example, side walls 45 can be made of black glass epoxy sheets (e.g., a FR4-type material) or black polyoxymethylene.

Figure 3:
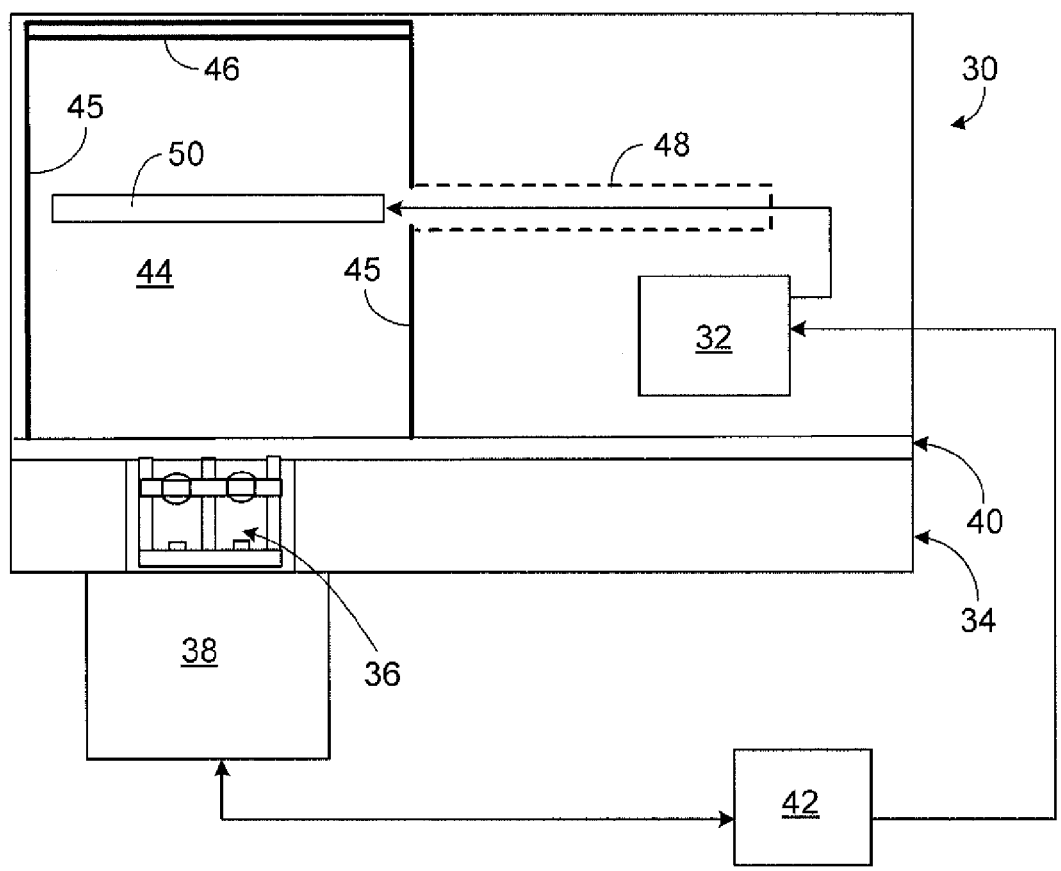
FIG. 3 is a diagram of the optical device testing unit showing the partition in a second position.

Adjacent space 44 has a horizontal opening 48 in which a moveable (e.g., slidable) partition 50 is stored. Partition 50 can be moved in response to a control signal from a controller 32 in testing unit 30, which in turn receives control signals from processing unit 42. In particular, partition 50 can be moved horizontally from opening 48 into space 44, as shown in FIG. 3. The width of partition 50 can be, for example, about the same as the width of space 44 such that, when the partition is moved into space 44, the partition extends substantially from opening 48 to the opposite interior wall 46 (see FIG. 3). Partition 50 subsequently can be moved back into opening 48. In some implementations, a commercially available grey reference card, such as the type used in digital photography, can be used as partition 50. Examples of such grey reference cards are commercially available from Mennon USA and can provide substantially uniform spectral reflectance, regardless of wavelength, color or intensity of the illumination. The grey reference card can be used for measuring the optical response of the module against a surface with well-defined reflectance properties.

By controlling the position of partition 50, different surfaces can be used during testing of optical device 36. Thus, some tests of optical device 36 can be performed while partition 50 is stored within opening 48, such that the optical device is tested while light is emitted toward the substantially non-reflective interior walls 46 of space 44, whereas other tests can be performed while partition 50 is located within space 44, thus providing a partially reflective surface for the testing.

Figure 4:
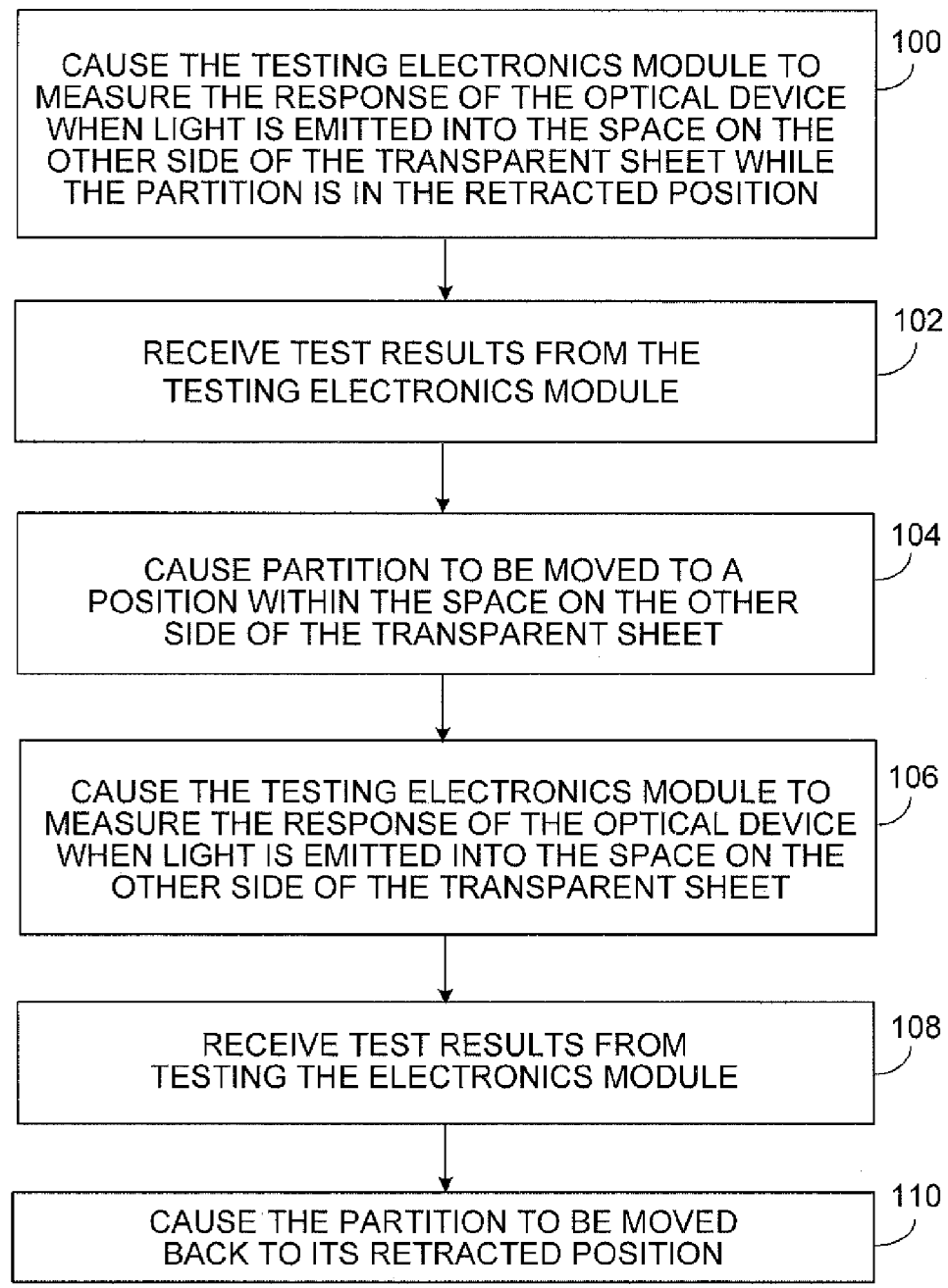
FIG. 4 is a flow chart of a method of testing an optical device.

Positioning of partition 50 (i.e., within opening 48 or within space 44) should be coordinated with the measurements to be performed by testing electronics module 38. This coordination can be accomplished by processing unit 42, which provides control signals to controller 32 as well as to testing electronics module 38. In some implementations, processing unit 42 provides control signals for the following operations. In a first operation, with partition 50 in the retracted position (see FIG. 2), processing unit 42 causes testing electronics module 38 to measure the response of optical device 36 when light is emitted into space 44 (FIG. 4, block 100). After receiving the test results from testing electronics module 38 (block 102), processing unit 42 causes partition 50 to be moved to a position within space 44 (see FIG. 3 and FIG. 4, block 104). Processing unit 44 then causes testing electronics module 38 to measure the response of optical device 36 when light is emitted into space 44 (block 106). After receiving the test results from testing electronics module 38 (block 108), processing unit 42 causes partition 50 to be moved back to its retracted position (block 110). The process then can be repeated for the next optical device.

The optical devices can be sorted based at least on part on the results of foregoing tests. Optical devices that fail to pass the tests or fail to meet specified user-defined requirements can be separated from devices that satisfy the tests. Performing such testing, for example, during production of the optical devices and sorting the devices prior to their being placed into the final end product or system can help avoid defective devices being placed into a final end product or system. This can help reduce costs associated with repairing an end product or system that would otherwise might be required.

In some implementations, the foregoing techniques can be combined example, with visual inspection of the optical devices 36 using optical machine vision. For example, automated optical inspection can be used to inspect the devices for scratches and defects prior to performing the tests described above using testing unit 30.

Although the testing unit 30 of FIG. 2 shows only a single moveable partition 50, other implementations can include multiple moveable partitions, each of which has different optical characteristics from the other partitions and which can be moved independently of the other partitions. For example, processing unit 42 can cause controller 32 to move each of partitions sequentially in and out of the optical path(s) of the optical device under test so as to simulate various conditions (e.g., different reflective surfaces). Test results indicative of the device's response (e.g., optical cross talk) can be obtained and analyzed using the different partitions, and a decision as to whether a particular optical device is acceptable can be determined based on the test results.

Although FIGS. 2 and 3 illustrate certain details of an example of an optical device 36, other types of optical devices can be tested using the described techniques. Such other optical devices may differ in one or more respects from the features of the illustrated optical device 36.

Other implementations are within the scope of the claims.

What is claimed is:

1. A testing unit for testing an optical device, the testing unit comprising:
 a device holder to hold the optical device;
 a testing electronics module adjacent the device holder, the testing electronics module including electrical contacts for connection to electrical contacts of the optical device and including electronics to measure a response of the optical device;
 a transparent cover adjacent the device holder;
 a wall located on a side of the transparent cover opposite that of the device holder, the wall having a first reflectivity;
 a movable partition that is slidable in and out of a region, wherein the partition has a reflectivity different from the wall; and
 a processing unit configured to:
  generate a control signal to cause the optical device to emit light that is transmitted through the transparent cover toward the wall;
  analyze a first response of the optical device;
  generate a control signal to cause the movable partition to be moved between the wall and the transparent cover;
  generate a control signal to cause the optical device to emit light that is transmitted through the transparent cover toward the movable partition;
  analyze a second response of the optical device; and
  determine whether or not the optical device passes a test based at least in part on analyzing the responses of the optical device.

2. The testing unit of claim 1 wherein the wall is substantially perpendicular to the transparent cover and is composed of a material that absorbs substantially all light from the optical device that impinges on the wall.

3. The testing unit of claim 1 wherein the partition is at least partially reflective.

4. The testing unit of claim 1 wherein the wall is composed of a black reference card.

5. The testing unit of claim 1 wherein the partition is composed of a grey reference card.

6. The testing unit of claim 1 wherein the transparent cover is composed of glass.

7. The testing unit of claim 1 wherein the transparent cover is composed of a polymer material.

8. The testing unit of claim 1 including a plurality of moveable partitions each of which is slidable into and out of the region independently of the other partitions, and wherein the partitions have different reflectivities from one another.

9. The testing unit of claim 1 wherein the wall is composed of a black reference card and the partition is composed of a grey reference card, wherein the processing unit is configured to provide control signals so that the black reference card is used for measuring leakage between a light emitting element and light detecting element in the optical device, and the grey reference card is used for measuring the optical response of the optical device against a surface with well-defined reflectance properties.

* * * * *